US008309708B2

(12) United States Patent
Hashaikeh et al.

(10) Patent No.: US 8,309,708 B2
(45) Date of Patent: Nov. 13, 2012

(54) CRYSTALLINE SULPHATED CELLULOSE II AND ITS PRODUCTION FROM SULPHURIC ACID HYDROLYSIS OF CELLULOSE

(75) Inventors: Raed Hashaikeh, Abu Dhabi (AE); Thomas Qiuxiong Hu, Vancouver (CA); Richard Berry, Notre-Dame-de-L'lle Perrot (CA)

(73) Assignee: FPInnovations, Pointe Claire, QC (CA)

( * ) Notice: Subject to any disclaimer, the term of this patent is extended or adjusted under 35 U.S.C. 154(b) by 127 days.

(21) Appl. No.: 12/774,298

(22) Filed: May 5, 2010

(65) Prior Publication Data

US 2010/0286387 A1  Nov. 11, 2010

Related U.S. Application Data

(60) Provisional application No. 61/213,092, filed on May 6, 2009.

(51) Int. Cl.
C08B 3/00 (2006.01)
C08B 5/00 (2006.01)
C08B 7/00 (2006.01)
C08B 13/00 (2006.01)

(52) U.S. Cl. ........................................................ 536/59
(58) Field of Classification Search .................... 536/59
See application file for complete search history.

(56) References Cited

U.S. PATENT DOCUMENTS

| | | | |
|---|---|---|---|
| 3,886,034 A | 5/1975 | Noreus |
| 4,064,342 A | 12/1977 | Saika et al. |
| 4,141,746 A | 2/1979 | Schweiger |
| 4,389,523 A | 6/1983 | Okajima et al. |
| 5,662,774 A | 9/1997 | Ekholm et al. |
| 2003/0024663 A1 | 2/2003 | Neogi et al. |
| 2003/0045707 A1 | 3/2003 | West et al. |

OTHER PUBLICATIONS

Xiang et al., Applied Biochemistry and Biotechnology, 2003, vol. 105-108, p. 505-514.*
French et al., in: Kirk-Othmer Encyclopedia of Chemical Technology, 4th Ed. vol. 5, 476-496, John Wiley & Sons, New York, N.Y. 1993.
Atalla and Nagel a) Science vol. 185: 522-523 (1974); b) Polymer Letters Edition vol. 12: 565-568 (1974).
Favier et al. Macromolecules 28: 6365-6367 (1995).
Samir et al. J. Phys. Chem. B 108: 10845-10852 (2004).
Revol et al. Liquid Crystals vol. 16(1): 127-134 (1994).
Dong et al. Cellulose 5: 19-32 (1998).
Bondeson et al. Cellulose 13: 171-180 (2006).
Araki et al. Colloids and Surfaces 142: 75-82 (1998).
Grunert and Winter Proceedings to 2nd Annual Partnerships for Environmental Improvement and Economic Development Conf., Syracuse, N.Y. USA, Apr. 9-11, (2000).
Sasaki et al. J. Agric. Food Chem. 51: 5376-5381 (2003).
Hermans and Weidinger J. Am. Chem. Soc. 2547-2552 (1946).
Gert Cellulose 3: 217-228 (1996).
Soep and Demoen Microchemical Journal vol. IV: 77-87 (1960).
Immergut et al. Monatsheft fur Chemie 84(2): 219-249 (1953).
Immergut et al. Monatsheft fur Chemie—pp. 1-34 (English translation), 1953.
International Search Report mailed Aug. 20, 2010.
Biochimica et Biophysica Acta, "X-Ray and Electron Microscope Studies of the Degradation of Celluloseby Sulphuric Acid", S.M. Mukherjee et al, vol. 10 (1953), pp. 499-511.
American Chemical Society, "Effect of Sulfate Groups from Sulfuric Acid Hydrolysis on the Thermal Degradation Behavior of Bacterial Cellulose", Maren Roman and William T. Winter, Biomacromolecules 2004, 5, pp. 1671-1677.
Carbohydrate Research, "Polysaccharide Sulfates. I. Cellulose Sulfate With a High Degree of Substitution", Richard G. Schweiger, Carbohyd. Res., 21 (1972) pp. 219-228.

* cited by examiner

*Primary Examiner* — Eric S Olson
*Assistant Examiner* — Zhengfu Wang
(74) *Attorney, Agent, or Firm* — Norton Rose Canada LLP (57) ABSTRACT

A method for producing crystalline sulphated cellulose II materials with relatively low degree of polymerization from spent liquors of sulphuric acid ($H_2SO_4$) hydrolysis of cellulose has been discovered. The method involves: 1) separating the spent liquors from the hydrolysed, acid-insoluble, cellulose I materials by dilution from, for example, a 64% $H_2SO_4$ hydrolysis medium to a residual sulphuric acid concentration of 10-50% with 0-40% $H_2SO_4$, followed by settling (or centrifuging) and decanting; 2) adding the diluted spent liquors to water or heating the diluted spent liquors at 30-80° C. for $\leq48$ h; and 3) recovering the recrystallized sulphated cellulose II materials with relatively low degree of polymerization either by filtration and washing or by washing and freeze drying. The method can be used to concurrently produce both crystalline, sulphated cellulose I and the crystalline, sulphated cellulose II materials.

16 Claims, 4 Drawing Sheets

CRYSTALLINE SULPHATED CELLULOSE II AND ITS PRODUCTION FROM SULPHURIC ACID HYDROLYSIS OF CELLULOSE

CROSS-REFERENCE TO RELATED APPLICATION

This application is related to U.S. Provisional Application 61/213,092 filed May 6, 2009 and the benefit under 35 USC 119(e) of such US Provisional Application is claimed.

BACKGROUND OF THE INVENTION i) Field of the Invention

This invention relates to crystalline sulphated cellulose II and its production especially from the sulphuric acid hydrolysis of cellulose, the invention also relates to the concurrent production of crystalline, sulphated cellulose I and sulphated cellulose II materials.

ii) Description of the Prior Art

Cellulose is the most abundant biopolymer on earth. It is the main component of higher plant cell walls, and it is also formed by some algae, fungi, bacteria, and a group of invertebrate marine animals, the tunicates [See reference by French et al.]. Native cellulose or cellulose from pulping of lignocellulosic materials is fibrous and consists of crystalline and amorphous domains of 1,4-linked β-D-glucose. The crystal structures (polymorphs) of cellulose vary depending on the source of cellulose and the method for its isolation. Because of the existence of various polymorphs, native cellulose has been named cellulose I in respect to its crystalline lattice. Various chemical and thermal treatments can change the lattice of cellulose I and generate other crystalline polymorphs. In terms of industrial applications, the cellulose II polymorph is the most important. It can be obtained by a transformation in the solid state such as in the mercerization process, or from regeneration from dissolved cellulose. Because the lattice of cellulose II is thermodynamically more stable, it cannot be converted back to cellulose I. One common method to characterize cellulose polymorphs is by X-ray diffraction studies. The major peaks in the X-ray diffractograms of crystalline cellulose materials are associated with reflections from the 101, 10$\bar{1}$ and 002 planes (with increasing 2θ values) corresponding to spacings of 6.01, 5.35 and 3.94 Å in the case of cellulose I and of 7.19, 4.42 and 4.06 Å in the case of cellulose II [See reference a) by Atalla and Nagel]. Native cellulose (cellulose I) derived from wood pulps typically shows poor resolution of the 101 and 10$\bar{1}$ peaks (peaks with lower 2θ values than the 002 peak). When cellulose I is converted to cellulose II by mercerization, an increase of 101 spacing and a decrease of 10$\bar{1}$ spacing occur, which leads to a lower 2θ value for the 101 peak and a higher 2θ value for the 10$\bar{1}$ peak for the mercerized material (cellulose II).

Hydrolysis of cellulose with sulphuric acid, $H_2SO_4$, in an aqueous medium under carefully controlled conditions gives cellulose whiskers or nanocrystals with excellent reinforcing ability in polymer nanocomposites [See references by Favier et al., and by Samir et al.]. Hydrolysis of cellulose with 64% $H_2SO_4$ at 45° C. for 20 minutes-4 h, 65° C. for 15 minutes, or 70° C. for 10 minutes, introduces negatively charged sulphate groups on cellulose microcrystallites and gives the microcrystallite suspensions that form, at sufficiently high concentrations, an ordered, chiral nematic liquid crystalline phase [See references by Revol et al., and by Dong et al.]. However, the yields of the cellulose microcrystallites that are capable of forming stable colloidal suspensions are only 34.4-48.1%.

Sulphate group can also be introduced to cellulose by treatment of cellulose with sulphur trioxide, $SO_3$ in N,N-dimethylformamide (DMF) [See reference by Schweiger]. Various methods for manufacturing sulphated cellulose materials using sulphur trioxide, $SO_3$ or Lewis base-$SO_3$ complex as the sulphating agent have been described in the patent literatures (See U.S. Pat. Nos. 4,064,342; 4,141,746; and 4,389,523). All these methods involve also the use of an organic reagent such as amine and/or an organic dispersant or solvent.

West and Westland have described various methods for making superabsorbent polymers including superabsorbent cellulose (See US Pat. Application Publication 20030045707 A1). One method for making the said superabsorbent cellulose comprises sulfating a cellulosic material with sulfuric acid, dissolving the sulfated cellulose in aqueous medium and precipitating the sulfated cellulose by adding a non-aqueous material (solvent) to the aqueous medium. Another method for making the said superabsorbent cellulose comprises sulfating a cellulosic material with sulfuric acid, dissolving the sulfated cellulose in aqueous medium, and regenerating the sulfated cellulose from the aqueous medium by drying off the water.

The content of sulphate groups introduced to the cellulose whiskers, nanocrystals or microcrystallites after the sulphuric acid hydrolysis of cellulose is usually assessed by sulphur elemental analysis or by conductometric titration of the materials. Sulphur (S) contents of 0.50-0.75% have been obtained on the microcrystallites obtained from 64% $H_2SO_4$ hydrolysis of Whatman No. 1 filter paper powder, while a sulphate group content of up to 393 mmol/kg which corresponds to a S content of 1.26% has been reported on the nanocrystals obtained with a yield of 23% and from the hydrolysis of Norway spruce microcrystalline cellulose (MCC) using 64.8% $H_2SO_4$ at 80° C. for 10 min [See reference by Bondeson, et al.].

Hydrolysis of bleached softwood kraft pulp or bacterial cellulose with 65% $H_2SO_4$ at 40 or 70° C. has been shown to give cellulose microcrystals or nanocrystals with the cellulose I polymorph [See references by Araki et al., and by Grunert and Winter].

Commercial production of cellulose II from cellulose I is achieved by the viscose method or the cuprammonium method [See reference by Sasaki et al.]. Laboratory preparation of cellulose II from cellulose I has been achieved by conversion of cellulose I to amorphous cellulose by grinding in a vibrating ball mill, and then by recrystallization of the amorphous cellulose by heating with $H_2O$ [See reference by Hermans and Weidinger]. Atalla and Nagel have prepared cellulose II by dissolution of cellulose powder in 85% phosphoric acid, $H_3PO_4$, and then by slow addition of the dissolved cellulose solution into $H_2O$ at room temperature [See reference a) by Atalla and Nagel]. Atalla and Nagel have also prepared cellulose II with higher crystallinity by mercerizing MCC with 23% NaOH and then by slow dilution of the mercerizing mixture with $H_2O$ and washing of the mixture at higher temperatures such as 80° C. [See reference b) by Atalla and Nagel]. Gert has reported the preparation of cellulose II by swelling of cellulose or MCC in 68% nitric acid, $HNO_3$, and then regenerating through pressing out the acid from the swollen cellulose, diluting with $H_2O$ to ~12% $HNO_3$ concentrating, heating, filtering and washing [See reference by Gert]. More recently, Sasaki et al. have described the preparation of cellulose II by solubilization of MCC in sub- or super-critical $H_2O$ at 320-400° C. (25-33 MPa), and then precipitation by decanting into $H_2O$ at 20° C. [See reference by Sasaki et al.].

Prior to the present invention, however, no soluble, sulphated cellulose has been recrystallized or recovered by simple addition of a solution of soluble, sulphated cellulose to water. In addition, no sulphated cellulose II has been isolated. Furthermore, no cellulose materials have been recovered from the spent liquors of $H_2SO_4$ hydrolysis of cellulose.

SUMMARY OF THE INVENTION

It is an object of this invention to provide crystalline, sulphated cellulose II with relatively low degree of polymerization (DP).

It is another object of this invention to provide a method for producing crystalline, sulphated cellulose II.

It is still another object of this invention to provide a process for producing crystalline, sulphated cellulose materials, especially crystalline, sulphated cellulose I from the sulphuric acid hydrolysis of cellulose, and concurrently crystalline, sulphated cellulose II, more especially from the spent liquor of sulphuric acid hydrolysis of cellulose.

It is still another object of this invention to provide a process for producing crystalline, sulphated cellulose II with relatively low degree of polymerization (DP).

In accordance with one aspect of the invention there is provided crystalline, sulphated cellulose II having a relatively low degree of polymerization (DP).

In accordance with another aspect of the invention there is provided a method for producing crystalline, sulphated cellulose II comprising: diluting a spent liquor from the sulphuric acid hydrolysis of cellulose, with an aqueous diluent, separating a diluted spent liquor from an acid-insoluble, crystalline sulphated cellulose I material, and generating crystalline, sulphated cellulose II from the separated, diluted spent liquor.

In accordance with still another aspect of the invention there is provided a process for producing crystalline, sulphated cellulose materials comprising:

forming an acid-insoluble, sulphated cellulose I material and a spent liquor from sulphuric acid hydrolysis of cellulose, diluting said spent liquor with an aqueous diluent, separating a diluted spent liquor from said acid-insoluble, sulphated cellulose material, generating crystalline, sulphated cellulose II from the separated, diluted spent liquor, and generating crystalline, sulphated cellulose I from the separated, acid-insoluble, sulphated cellulose material.

In accordance with yet another aspect of the invention there is provided a process for producing crystalline, sulphated cellulose II having a relatively low degree of polymerization (DP) comprising:

dissolution of cellulose in concentrated sulphuric acid to form a solution of dissolved cellulose material comprising sulphated cellulose material, and generating crystalline, sulphated cellulose II from said solution by dilution of said solution with an aqueous diluent.

It has now been discovered that crystalline sulphated cellulose II with relatively low degree of polymerization (DP) can be isolated from spent liquors of $H_2SO_4$ hydrolysis of cellulose such as fully-bleached kraft pulp fibres. The isolation method involves: 1) separating the spent liquors from the hydrolysed, acid-insoluble cellulose I materials by dilution from, for example, a 64% $H_2SO_4$ hydrolysis medium to a residual $H_2SO_4$ concentration of 10-50% with 0-40% $H_7SO_4$, followed by settling (or centrifuging) and decanting; 2) adding the diluted spent liquors to water or heating the diluted spent liquors at 30-80° C. for ≦48 h; and 3) recovering the precipitated sulphated cellulose II materials with relatively low DP either by filtration and washing or by washing and freeze drying. The method can be used to concurrently produce both crystalline, sulphated cellulose I and crystalline, sulphated cellulose II materials with relatively low DP.

It has also been discovered that crystalline sulphated cellulose II with relatively low DP can be isolated from dissolved cellulose solutions in sulphuric acid, added to a known volume of deionized (DI) $H_2O$ over a known period of time at a given temperature (20-80° C.).

The crystalline sulphated cellulose II materials with relatively low DP of the present invention can be used as potential antiviral agents such as an anti-human-immunodeficiency-virus (anti-HIV) agent, or multifunctional excipients (a binder, filler and disintegrant) for the production of drug tablets or capsules. They may be used for the microencapsulation of biological objects/living cells in the treatment of various diseases such as diabetes. They can also be used for the production of films and fibres, or as strengthening/reinforcing components for the production of polymer nanocomposites or novel paper products.

DETAILED DESCRIPTION OF THE INVENTION

The $H_2SO_4$ hydrolysis of cellulose to form cellulose whiskers, microcrystallites or nanocrystals is typically conducted by mixing the cellulose with concentrated (~64%) $H_2SO_4$ at a temperature of 45-65° C. The minimum hydrolysis time needed to produce the microcrystallites at this concentration is 20 minutes at 45° C. and 15 minutes (i.e. 0.25 h) at 65° C. [See reference by Dong et al.]. The hydrolysis produces the acid-insoluble, sulphated cellulose whiskers, microcrystallites or nanocrystals by degrading and solubilizing the structurally more vulnerable amorphous domains of cellulose. The spent liquors from such $H_2SO_4$ hydrolysis consist of residual $H_2SO_4$ and the soluble cellulose degradation products and other by-products of the hydrolysis. The acid-insoluble, sulphated cellulose materials with yields typically lower than 50% are separated from the spent liquors by settling (or centrifugation), decanting and repeated washing or by filtration and washing. No method has been reported in the literature to recover cellulose II from the spent liquors of this type of hydrolysis.

According to the present invention, diluting the spent liquors from concentrated (56-68%) $H_2SO_4$ hydrolysis of cellulose with an aqueous diluent, more preferably 0-40% $H_2SO_4$ solution, separating the diluted spent liquors from the acid-insoluble, sulphated cellulose materials, and adding the diluted spent liquors to water (or diluting the spent liquors with water) or heating them at 30-80° C. for ≦48 h will allow the generation, more specifically, recrystallization and isolation of sulphated cellulose II materials with relatively low DP (typically DP≦~60) from the spent liquors. The separated, acid-insoluble, sulphated cellulose materials can be, if needed, further hydrolyzed, without addition of extra $H_2SO_4$ or with the addition of $H_2SO_4$ to bring the $H_2SO_4$ acid concentration up to 64-68%, to give highly-crystalline, sulphated cellulose I materials in different forms such as sulphated cellulose whiskers, microcrystallites, nanocrystals or stable colloidal suspensions. Thus, the present invention provides a method for the concurrent production of crystalline, sulphated cellulose I and sulphated cellulose II materials from the $H_2SO_4$ hydrolysis of cellulose. The volume of the said aqueous diluent is typically 0.2-5.0 times the volume of the said spent liquor, and more preferably, 0.5-3.0 times the volume of the said spent liquor. The volume of water to which the said diluted spent liquor is added to is typically 0.5-3.0 times the volume of the said diluted spent liquor.

According to the present invention, crystalline, sulphated cellulose II materials with relatively low DP can also be produced by dissolution of cellulose in concentrated sulphuric acid (>64%) at a known temperature for a known period of time, followed by dilution of the dissolved cellulose solutions with water, or by addition of the dissolved cellulose solutions to water over a known period of time at a given temperature (20-80° C.).

Figure 1:
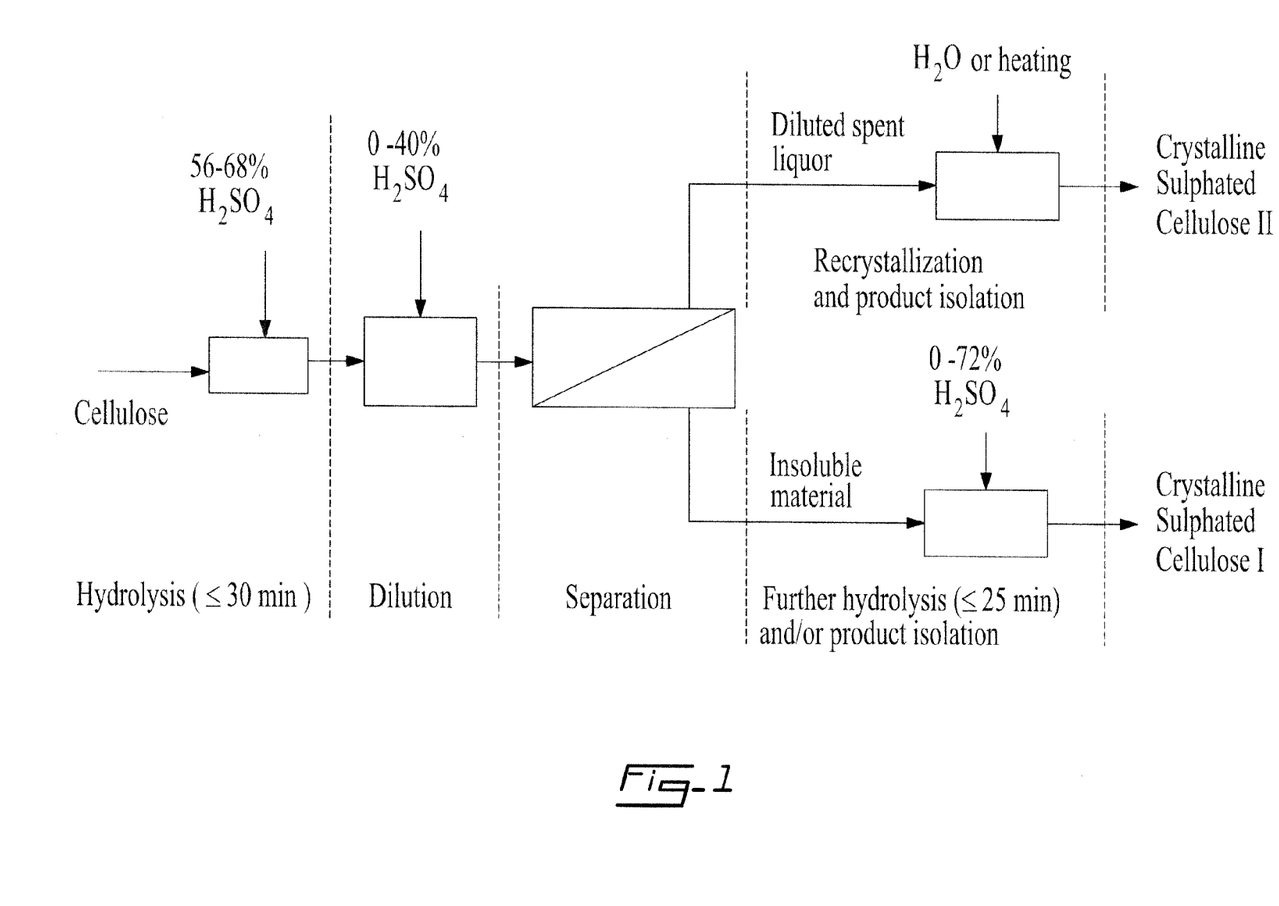
FIG. 1 Flow diagram of the isolation of crystalline, sulphated cellulose I and crystalline, sulphated cellulose II materials according to the current invention.

The yield, the sulphate group content, the DP, and the morphological and other chemical properties of the said cellulose I and the said cellulose II materials isolated according to the present invention depend on the starting cellulose materials used, the conditions (e.g. time, temperature, $H_2SO_4$ concentration) of the hydrolysis of cellulose, the $H_2SO_4$ concentration and volume used for the dilution of the spent liquor, and the conditions for the treatment of the diluted spent liquor. For the concurrent production of cellulose I and cellulose II materials, the hydrolysis is preferably performed at 56-68% $H_2SO_4$ at 40-65° C. for 5-30 minutes. The dilution is preferably performed using 0-40% $H_2SO_4$ and the recrystallization of the soluble cellulose materials in the diluted spent liquor is preferably performed by slowly adding the spent liquor to water at 20-80° C. or by heating it at 30-80° C. for ≦48 h. FIG. 1 shows a flow diagram of the steps involved in the isolation of crystalline, sulphated cellulose I and crystalline, sulphated cellulose II materials according to the current invention.

Cellulose in the present invention includes, but is not limited to cellulose from pulping and bleaching of lignocellulosic materials such as fully bleached Kraft pulp or sulfite pulp. It can also be, for example, bacterial cellulose, tunicate cellulose, or microcrystalline cellulose.

Crystalline, sulphated cellulose I materials in the present invention include, but are not limited to, sulphated cellulose whiskers, microcrystallites and nanocrystals, nanocrystalline cellulose (NCC), and stable colloidal cellulose suspension.

Crystalline, sulphated cellulose II materials in the present invention are typically soluble in more concentrated sulphuric acid solutions but are insoluble in water or in less concentrated sulphuric acid solutions.

An aqueous diluent in the present invention includes, but is not limited to 0-40% aqueous sulphuric acid ($H_2SO_4$).

The present invention is illustrated by, but not limited to, the following examples:

General Procedure A: Isolation of Crystalline, Sulphated Cellulose I and Diluted Spent Liquor from Sulphuric Acid Hydrolysis of Cellulose A known amount of cellulose such as a fully-bleached kraft pulp is milled to pass through a 0.5-mm screen in a Wiley mill (Thomas-Wiley Lab mill, Model 4, Thomas Scientific, USA). A known volume of $H_2SO_4$ at a known concentration (56-68%) is heated to a desired temperature (40-65° C.) and added to the milled cellulose under stirring with an impeller at 200 rpm. The mixture is heated at the desired temperature (40-65° C.) for a known period of time (5-30 minutes) under stirring with an impeller at 500-600 rpm. At the end of heating, a known volume of deionized (DI) $H_2O$ or $H_2SO_4$ (concentration≦40%) is added under stirring with an impeller at 500-600 rpm. The suspension is centrifuged or allowed to settle over a known period of time. A known volume of the clear, top layer is decanted as the spent liquor.

All or a known portion of the remaining thick suspension is diluted with a known amount of cold (10° C.) DI $H_2O$ to give a residual $H_2SO_4$ concentration of 4-25% (residual $H_2SO_4$ concentration is calculated based on no $H_2SO_4$ consumption during hydrolysis), or is further hydrolyzed without or with the addition of a known amount of 0-72% sulphuric acid at a desired temperature (40-65° C.) for a known period of time before dilution with a known amount of cold (10° C.) DI $H_2O$ to give a residual $H_2SO_4$ concentration of 4-25%. The suspension is centrifuged, or allowed to settle overnight and then centrifuged, or allowed to settle over a known period of time. Most of the clear, top layer is decanted off The remaining thick suspension is washed twice by adding the same amount of DI $H_2O$ as that which has been decanted, followed by mixing, centrifuging (or settling) and decanting of the top layer. After the final decanting, the thick white suspension is placed inside dialysis membrane tubes (or a dialysis module) and dialyzed against slow running tap water or DI $H_2O$ for three days. After dialysis, the yield (yield of all the insoluble sulphated cellulose I) is determined by withdrawing and determining the oven-dried weight of a known amount of a small sample, and by taking into account whether all or only a portion of the thick suspension is used. A freeze-dried sample and an oven-dried sample are prepared. The sulphur (S) content of the freeze-dried sample is determined by titration after combustion according to a literature procedure [See reference by Soep and Demoen]. An X-ray diffractogram of the oven-dried sample is obtained on an X-ray diffractometer (Siemens, Bruker AXS D5000) using Co—$K_\alpha$ radiation. The degree of polymerization (DP) of the freeze-dried sample or the starting cellulose is, when needed, determined from the intrinsic viscosity [η] in $cm^3/g$ measured according to SCAN-CM 15:99 test method by means of the formula, $DP^{0.905}=0.75$ [η]. The formula is derived from the equation [η]=$1.33\times10^{-4}$ $M^{0.905}$ [See reference by Immergut et al.], where M is the molecular weight and [q] is the intrinsic viscosity in 100 mL/g.

General Procedure B: Isolation of Crystalline, Sulphated Cellulose II from the Diluted Spent Liquor by Addition to Water A known amount of the spent liquor is poured into a known amount of water or DI $H_2O$ under manual mixing with a glass rod to give a residual $H_2SO_4$ concentration of, unless otherwise specified, 19.2% (calculated based on no $H_2SO_4$ consumption during the hydrolysis). Upon the addition of the spent liquor into the $H_2O$, a white precipitate is formed. The mixture of the white precipitate and the solution is centrifuged (or allowed to settle), followed by decanting of a known volume of the clear top layer. A known volume (typically the same as the volume of top layer decanted) of DI $H_2O$ is added, followed by mixing, centrifuging (or settling) and decanting of the top layer. The same washing procedure is repeated one more time. After the final decanting, the thick white suspension is placed inside dialysis membrane tubes (or a dialysis module) and dialyzed against slow running tap water or DI $H_2O$ for three days. After dialysis the suspension is freeze-dried to give the recrystallized sulphated cellulose II. The yield of the material is calculated based on the volume of the spent liquor decanted after hydrolysis, dilution and centrifugation. The sulphur (S) content of the freeze-dried material is determined by titration after combustion according to a literature procedure [See reference by Soep and Demoen]. An oven-dried sample is prepared. X-ray diffractogram of the oven-dried sample is obtained on an X-ray diffractometer (Siemens, Bruker AXS D5000) using Co—$K_\alpha$ radiation. DP of the freeze-dried sample, when needed, is determined using the same method as that described in General Procedure A.

General Procedure C: Isolation of Crystalline, Sulphated Cellulose II from the Diluted Spent Liquor by Heating A known amount of the diluted spent liquor is filtered and then heated at, unless otherwise specified, 45° C. for 46 h. Upon heating, a white precipitate is formed. A known amount of the clear top layer (typically half of the total volume) is decanted off. The remaining residue with the white precipitate is transferred into a dialysis membrane tube, and dialyzed against tap water or DI $H_2O$ for 3 days. During dialysis the white precipitate settles down at the bottom of the membrane leaving a clear top layer. A known amount of the clear top layer (typically ¾ of the total volume) is decanted off and replaced with the same amount of DI $H_2O$. This displacement washing is repeated two more times. After the final decanting, the remaining suspension is freeze-dried to give the recrystallized sulphated cellulose II. The yield of the material is calculated based on the volume of the spent liquor decanted after hydrolysis, dilution and centrifugation. Sulphur (S) content of the freeze-dried material is determined by titration after combustion according to a literature procedure [See reference by Soep and Demoen]. An oven-dried sample is prepared. An X-ray diffractogram of the oven-dried sample is obtained on an X-ray diffractometer (Siemens, Bruker AXS D5000) using Co—$K_\alpha$ radiation. The DP of the freeze-dried sample is, when needed, determined using the same method as that described in General Procedure A.

General Procedure D: Isolation of Crystalline, Sulphated Cellulose II from the Dissolved Solution of Cellulose in Sulphuric Acid A known amount of cellulose such as a fully-bleached kraft pulp is milled to pass through a 0.5-mm screen in a Wiley mill (Thomas-Wiley Lab mill, Model 4, Thomas Scientific, USA). A known volume of $H_2SO_4$ at a known concentration (>64%) is added to the milled cellulose at room temperature (~23° C.) under stirring with an impeller at 200 rpm. The mixture is stirred with an impeller at 500-600 rpm for a known period of time (5-30 minutes) to give a clear, dissolved cellulose solution. A known volume of deionized (DI) $H_2O$ is added to the cellulose solution under stirring with an impeller at 500-600 rpm, or the cellulose solution is added to a known volume of DI $H_2O$ over a known period of time at a given temperature (20-80° C.) to form a white precipitate. The mixture of the white precipitate and the solution is centrifuged or allowed to settle. Most of the clear top layer (typically 80-90% of the total volume) is decanted off. The remaining thick white suspension is diluted with a known amount of DI $H_2O$, mixed and centrifuged (or allowed to settle), followed by decanting of the same or close to the same volume of the clear top layer as that of the DI $H_2O$ used for the dilution. The same dilution, mixing, centrifuging (or settling) and decanting is repeated twice. After the final decanting, the thick white suspension is placed inside dialysis membrane tubes (or a dialysis module) and dialyzed against slow running tap water or DI $H_2O$ for 3 days. After dialysis, the yield of the white precipitate/recrystallized material is determined by withdrawing and determining the oven-dried weight of a known amount of a small sample. A freeze-dried sample and an oven-dried sample are prepared. The sulphur (S) content of the freeze-dried sample is determined by titration after combustion according to a literature procedure [See reference by Soep and Demoen]. A X-ray diffractogram of the oven-dried sample is obtained on an X-ray diffractometer (Siemens, Bruker AXS D5000) using Co—$K_\alpha$ radiation. DP of the freeze-dried sample is determined, when needed, using the same method as that described in General Procedure A.

EXAMPLE 1

29.2 g (oven-dried basis) of a fully-bleached, commercial softwood kraft pulp (DP=972±43) is milled and hydrolyzed, according to General Procedure A disclosed above, with 265 mL of 64% $H_2SO_4$ at 45° C. for 10 minutes to give, after dilution with 545 mL of 40% $H_2SO_4$ (to give a residual $H_2SO_4$ concentration of 48%), centrifugation and decanting, 425 mL of a clear spent liquor and 350 mL of a thick suspension.

175 mL of the thick suspension is diluted with 1300 mL of cold DI $H_2O$ to give a residual $H_2SO_4$ concentration of 5.7% and then processed according to General Procedure A disclosed above to give 7.04 g of the acid-insoluble material. The yield of the acid-insoluble material is determined to be 48.2% based on 350 mL of the thick suspension isolated. The S content of the acid-insoluble material is determined to be 0.95%. The DP of the acid-insoluble material is determined to be 68±6.

A portion (400 mL) of the spent liquor is poured into 600 mL DI $H_2O$ to give a white precipitate according to General Procedure B disclosed above. The mixture of the white precipitate and the solution is processed, according to General Procedure B disclosed above and with the volume of the clear top layer decanted and that of DI $H_2O$ used being 600 mL, to give 4.36 g of the recrystallized material. The yield of the recrystallized material is calculated to be 15.9% based on a decanted spent liquor of 425 mL. The S content of the material is determined to be 1.09%. The DP of the recrystallized material is determined to be 20±2.

Figure 2:
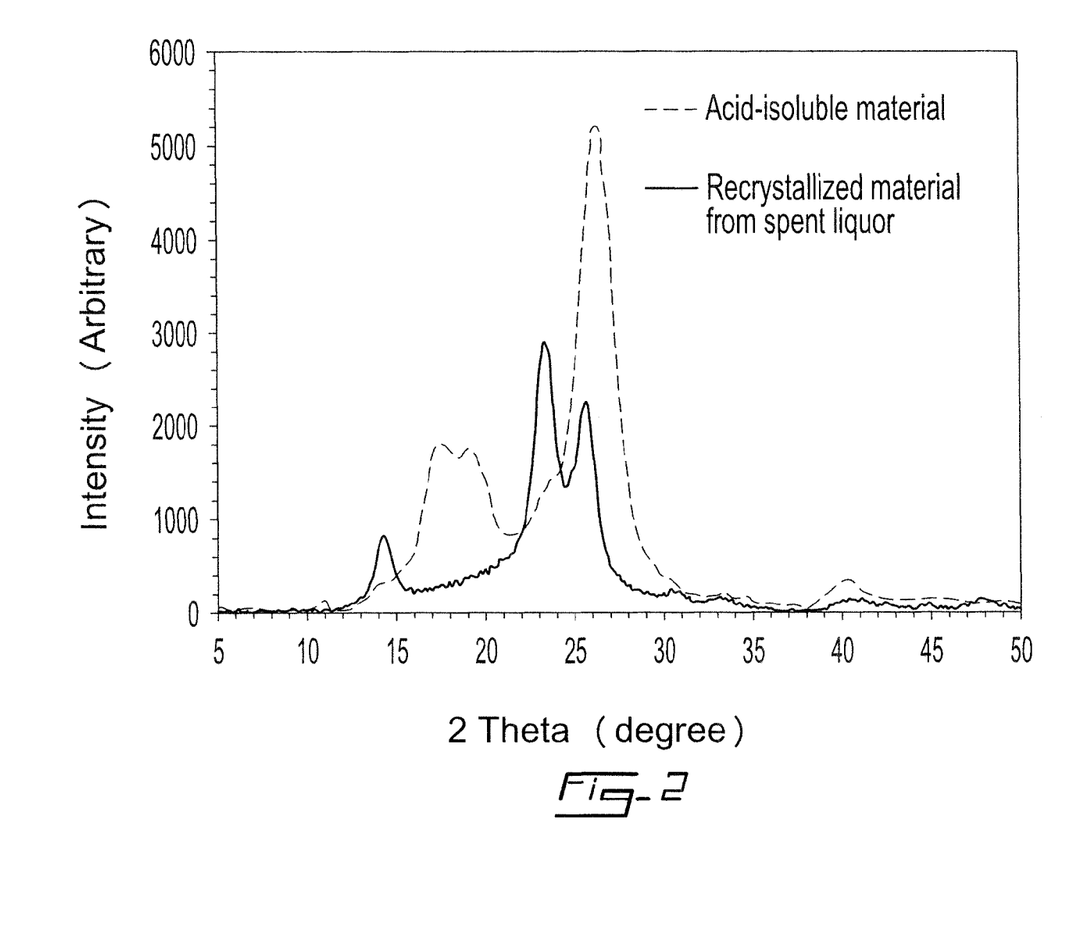
FIG. 2 X-ray diffractograms of the acid-insoluble material (- -) showing a cellulose I diffraction pattern and the recrystallized material from the spent liquor (-) showing a cellulose II diffraction pattern.

FIG. 2 shows X-ray diffractograms of the acid-insoluble material (- -) and the recrystallized material from the spent liquor. The X-ray diffractogram of the acid-insoluble material shows a diffraction pattern with 2θ (2 Theta) peaks of 17.8, 19.1 and 26.4° that are characteristic of cellulose I. The X-ray diffractogram of the recrystallized material shows a diffraction pattern with 2θ (2 Theta) peaks of 14.4, 23.4 and 25.7° that are characteristic of cellulose II.

EXAMPLE 2

29.1 g (oven-dried basis) of a fully-bleached, commercial softwood kraft pulp is milled and hydrolyzed, according to General Procedure A disclosed above, with 265 mL of 64% $H_2SO_4$ at 45° C. for 25 minutes to give, after dilution with 635 mL of DI $H_2O$ (to give a residual $H_2SO_4$ concentration of 18.8%), centrifugation and decanting, 400 mL of a clear spent liquor and 500 mL of a thick suspension.

The thick suspension is diluted with 500 mL of cold DI $H_2O$ and then processed/washed according to General Procedure A disclosed above to give the acid-insoluble material. The yield of the material is determined to be 32.9%. The S content of the acid-insoluble material is determined to be 0.86%.

The spent liquor (400 mL) is filtered and then heated at 45° C. for 46 h according to General Procedure C disclosed above. At the end of heating, 200 mL of the clear top layer is decanted off. The remaining residue with the white precipitate is transferred into a dialysis membrane, dialyzed and washed according to General Procedure C disclosed above with the volume of clear top layer decanted and that of the DI $H_2O$ added being 150 mL. After the final decanting, 50 ml of the remaining suspension is freeze-dried to give 70 mg of the recrystallized material. The yield of the recrystallized material is calculated to be 0.24% based on a decanted spent liquor of 400 mL. The S content of the material is determined to be 0.70%.

Figure 3:
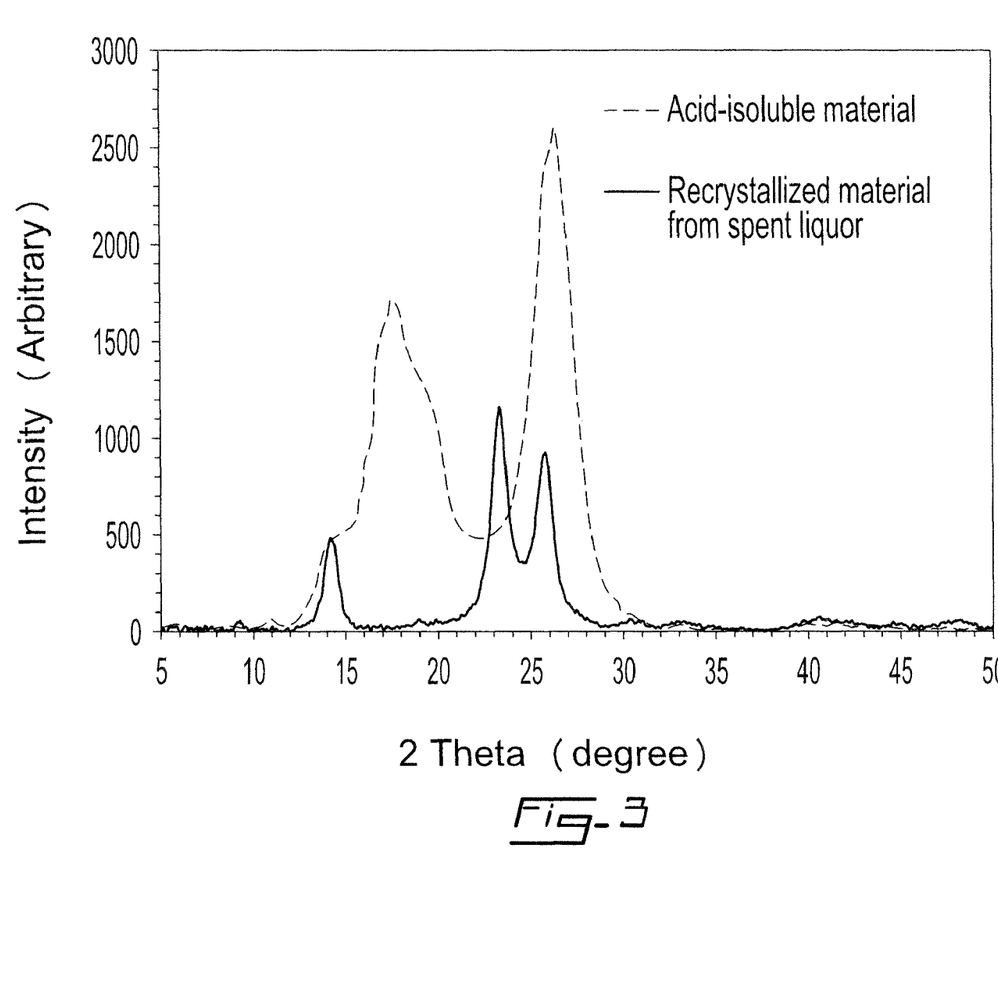
FIG. 3 X-ray diffractograms of the acid-insoluble material (- -) showing a cellulose I diffraction pattern and the recrystallized material from the spent liquor (-) showing a cellulose II diffraction pattern.

FIG. 3 shows X-ray diffractograms of the acid-insoluble material (- -) and the recrystallized material from the spent liquor (-). The X-ray diffractogram of the acid-insoluble material has a diffraction pattern that is characteristic of cellulose I, while the X-ray diffractogram of the recrystallized material has a diffraction pattern that is characteristic of cellulose II.

EXAMPLE 3

Figure 4:
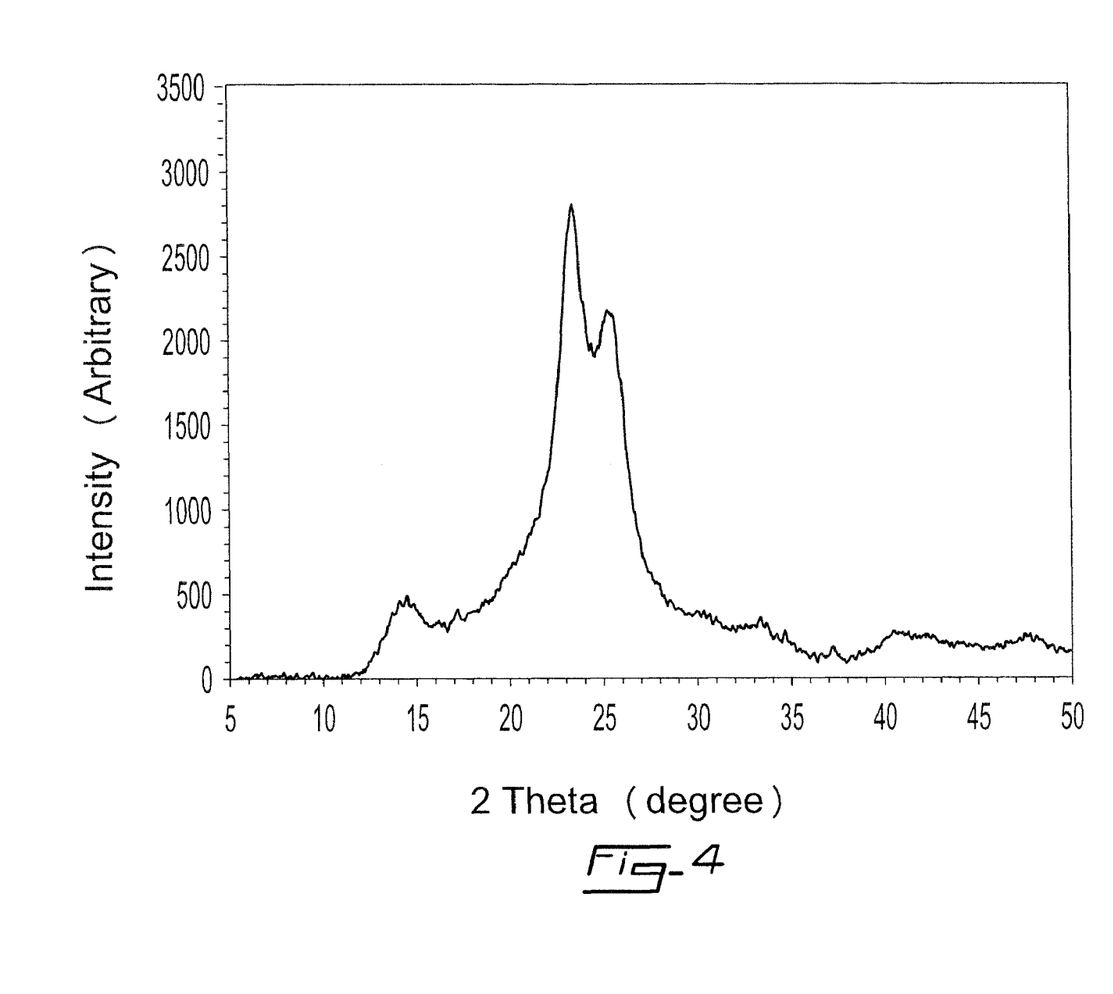
FIG. 4 X-ray diffractogram of the recrystallized material from the clear, dissolved cellulose solution after hydrolysis with 72% $H_2SO_4$, showing a cellulose II diffraction pattern.

24.5 g (oven-dried basis) of a fully-bleached, commercial softwood kraft pulp (DP=972±43) is milled and hydrolyzed, according to General Procedure D disclosed above, with 250 mL of 72% $H_2SO_4$ at room temperature (~23° C.) for 25 minutes to give a clear, dissolved cellulose solution. The cellulose solution is diluted with 3 L of cold (10° C.) DI $H_2O$ to produce white precipitate according to General Procedure D disclosed above. The mixture of the white precipitate and the solution is centrifuged. 2.75 L of the clear top layer is decanted off to give approximately 500 mL of a thick white suspension according to General Procedure D disclosed above. The white suspension is diluted with 400 mL DI $H_2O$, mixed and centrifuged, followed by decanting of 400 mL of clear top layer. The same dilution, mixing, centrifuging and decanting is repeated twice, and the thick white suspension (500 mL) after the final decanting is dialyzed according to General Procedure D disclosed above. The yield of the white precipitate/recrystallized material is determined to be 73.6%. The S content of the material is determined to be 1.18%. The DP of the recrystallized material is determined to be 43±3. FIG. 4 is the X-ray diffractogram of the recrystallized material and it shows a diffraction pattern that is characteristic of cellulose II.

REFERENCES CITED

Us Patent Documents

| | | |
|---|---|---|
| 4,064,342 | December 1977 | Saika et al. |
| 4,141,746 | February 1978 | Schweiger |
| 4,389,523 | June 1983 | Okajima et al. |

US Patent Applications

| | | |
|---|---|---|
| 2003/0045707 A1 | March 2003 | West et al. |

Other Publications

French et al., in: *Kirk-Othmer Encyclopedia of Chemical Technology*, 4th Ed. V.5, 476-496, John Wiley & Sons, New York, N.Y. 1993.
Atalla and Nagel a) *Science* 185: 522-523 (1974); b) *Polymer Letters Edition* 12: 565-568 (1974).
Favier et al. *Macromol.* 28: 6365-6367 (1995).
Samir et al. *J. Phys. Chem. B* 108: 10845-10852 (2004).
Revol et al. *Liquid Crystals* 16(1): 127-134 (1994).
Dong et al. *Cellulose* 5: 19-32 (1998).
Schweiger *Carbohydrate Res.* 21: 219-228 (1972).
Bondeson, et al. *Cellulose* 13: 171-180 (2006).
Araki et al. *Colloids and Surface* 142: 75-82 (1998).
Grunert and Winter *Proceedings to 2nd Annual Partnerships for Environmental Improvement and Economic Development Conf.*, Syracuse, N.Y. USA, Apr. 9-11 (2000).
Sasaki et al. *J. Agric. Food Chem.* 52: 5376-5381 (2003).
Hermans and Weidinger *J. Am. Chem. Soc.* 2547-2552 (1946).
Gert *Cellulose* 3: 217-228 (1996).
Soep and Demoen *Microchemical Journal IV:* 77-87 (1960).
Immergut et al. *Monatsheft fur Chemie* 84(2): 219-249 (1953).

The invention claimed is:

1. A method for producing crystalline, sulphated cellulose II comprising:
   diluting a spent liquor from the hydrolysis of cellulose of a fully bleached kraft pulp or sulfite pulp with 56-68% sulphuric acid at 40-65° C. for 5-30 minutes, with an aqueous diluent selected from the group consisting of water and up to 40% aqueous sulphuric acid,
   separating a diluted spent liquor from an acid-insoluble, sulphated cellulose I material,
   and
   generating crystalline, sulphated cellulose II from the separated, diluted spent liquor.

2. The process according to claim 1, wherein said cellulose is a fully bleached Kraft pulp.

3. The process according to claim 1, wherein the aqueous diluent is up to 40% aqueous sulphuric acid.

4. The process according to claim 1, wherein said generating of crystalline, sulphated cellulose II comprises admixing the separated, diluted spent liquor with water.

5. The process according to claim 1, wherein said cellulose is a fully bleached sulfite pulp.

6. The method according to claim 1, wherein the crystalline, sulphated cellulose II has a (DP)≦60.

7. The method according to claim 1, wherein said generating comprises heating the separated, diluted spent liquor at 30 to 80° C. for up to 48 hours.

8. A process for producing crystalline, sulphated cellulose materials comprising:
   forming an acid-insoluble, sulphated cellulose material and a spent liquor from hydrolysis of cellulose with 56-68% sulphuric acid at 40-65° C. for 5-30 minutes, wherein said cellulose is a fully bleached kraft pulp,
   diluting said spent liquor with an aqueous solution of 0-40% sulphuric acid as an aqueous diluent,
   separating a diluted spent liquor from an acid-insoluble, sulphated cellulose material,
   generating crystalline, sulphated cellulose II from the separated, diluted spent liquor,
   and
   generating crystalline, sulphated cellulose I from the separated, acid-insoluble, sulphated cellulose material.

9. The method according to claim 8, wherein the crystalline, sulphated cellulose II has a (DP)≦60.

10. The method according to claim 9, wherein said generating comprises admixing the separated, diluted spent liquor with water.

11. The method according to claim 9, wherein said generating comprises heating the separated, diluted spent liquor at 30 to 80° C. for up to 48 hours.

12. A The process according to claim 8, wherein said generating of crystalline, sulphated cellulose I comprises isolating the separated, acid-insoluble, sulphated cellulose material to produce said crystalline, sulphated cellulose I.

13. A The process according to claim 8, wherein said generating of crystalline, sulphated cellulose I comprises further hydrolysing the separated, acid-insoluble, sulphated cellulose material at a sulphuric acid concentration up of 4% to 68% and then isolating the acid-insoluble, sulphated cellulose material to produce said crystalline, sulphated cellulose I.

14. The process according to claim 8, wherein the aqueous diluent is up to 40% aqueous sulphuric acid.

15. The process according to claim 8, wherein said generating of crystalline, sulphated cellulose II comprises admixing the separated, diluted spent liquor with water.

16. The process according to claim 8, wherein said generating of crystalline, sulphated cellulose II comprises heating the separated, diluted spent liquor at 30 to 80° C. for up to 48 hours.

* * * * *